(12) United States Patent
Mhaske et al.

(10) Patent No.: US 12,145,931 B2
(45) Date of Patent: Nov. 19, 2024

(54) SUBSTITUTED PYRROLO[2,3-C]QUINOLINES AS ANTIMALARIALS

(71) Applicant: COUNCIL OF SCIENTIFIC AND INDUSTRIAL RESEARCH, New Delhi (IN)

(72) Inventors: Santosh Baburao Mhaske, Pune Maharashtra (IN); Jyoti Pankaj Mahajan, Pune Maharashtra (IN); Shanmugam Dhanasekaran, Pune Maharashtra (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 1007 days.

(21) Appl. No.: 16/971,232

(22) PCT Filed: Feb. 19, 2019

(86) PCT No.: PCT/IN2019/050130
§ 371 (c)(1),
(2) Date: Aug. 19, 2020

(87) PCT Pub. No.: WO2019/159202
PCT Pub. Date: Aug. 22, 2019

(65) Prior Publication Data
US 2021/0087187 A1    Mar. 25, 2021

(30) Foreign Application Priority Data
Feb. 19, 2018   (IN) .............................. 201811006181

(51) Int. Cl.
| A61K 31/437 | (2006.01) |
| A61P 33/06 | (2006.01) |
| B01D 5/00 | (2006.01) |
| B01D 11/04 | (2006.01) |
| C07D 471/04 | (2006.01) |

(52) U.S. Cl.
CPC ............ C07D 471/04 (2013.01); A61P 33/06 (2018.01); B01D 5/0063 (2013.01); B01D 11/0492 (2013.01)

(58) Field of Classification Search
CPC ........................... A61K 31/437; C07D 471/04
USPC .............................................. 514/291; 546/84
See application file for complete search history.

(56) References Cited

U.S. PATENT DOCUMENTS

| 5,459,272 A | 10/1995 | Novotny et al. |
| 9,518,051 B2 | 12/2016 | Mhaske et al. |

OTHER PUBLICATIONS

Panarese, et al. Organic Letters, 14(22), 2012, 5808-5810.*
Niall J. Dickinson, "The Application of Iminium Ions to the Synthesis of Biologically Active Molecules", Ph.D. Thesis, 2013 scheme 78, 80; compounds 341-344, 348-351, pp. 72-73.
Mahajan et al. 2012. Pd-Catalyzed Imine Cyclization: Synthesis of Antimalarial Natural Products Aplidiopsamine A, Marinoquinoline A, and Their Potential Hybrid NCLite-M1, Org. Lett, 14(22):5804-5807, Oct. 24, 2012. whole document.
Dickinson, University of Southampton Research Repository Eprints Soton, The Application of Iminium Ions to the Synthesis of Biologically Active Molecules, pp. 1-337.
Okaya, et al., Journal of Natural Products, Marinoquinolines Pyrroloquinolines from Ohtaekwangia Kribbensis (Bacteroidetes), pp. 603-606.
Mahajan, et al., Synthesis of Antimalarial Natural Products Aplidiopsamine A, Marinoquinoline A, and Their Potential Hybrid NC-Lite-M1, Organic Letters 2012, vol. 14 No. 22, pp. 5804-5807.

\* cited by examiner

*Primary Examiner* — Douglas M Willis
(74) *Attorney, Agent, or Firm* — ArentFox Schiff LLP

(57) ABSTRACT

The present invention relates to an antimalarial heterocyclic compound of formula I, dimers thereof and process for the preparation thereof. Further, the present invention relates to a pharmaceutical composition of heterocyclic compound of formula I, dimers thereof for treating malarial infection.

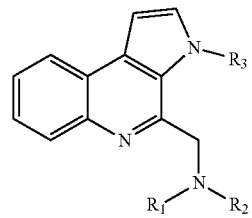

Formula I

5 Claims, 1 Drawing Sheet

SUBSTITUTED PYRROLO[2,3-C]QUINOLINES AS ANTIMALARIALS

This application is a 35 U.S.C. § 371 National Phase of PCT Application No. PCT/IN2019/050130, filed Feb. 19, 2019, which claims priority to Indian Application No. 201811006181, filed Feb. 19, 2018, the disclosures of which are hereby incorporated by reference herein.

FIELD OF THE INVENTION

The present invention relates to an antimalarial heterocyclic compound of formula I, dimers or a pharmaceutically acceptable salt thereof. Particularly, present invention relates to a process for the preparation of antimalarial heterocyclic compound of formula I, dimers or a pharmaceutically acceptable salt thereof. More particularly, the present invention relates to a pharmaceutical composition comprising heterocyclic compound of formula I, dimers or pharmaceutically acceptable salt thereof for treating or preventing malarial infection in a subject in need thereof comprises of administering a therapeutically effective amount of a compound formula I, dimers or pharmaceutically acceptable salt thereof.

BACKGROUND AND PRIOR ART OF THE INVENTION

Malaria a life threatening disease caused by bite of infected female anopheles mosquito. According to World health Organization (WHO) reports there are about 400 000 deaths caused globally by malaria. Malaria mainly caused by four species of protozoan i.e. *Plasmodium falciparum, P. vivax, P. ovale, P. malariae*. Alkaloids are highly important pharmacophores and currently available methods for the synthesis of substituted pyridine based alkaloids are tedious, lengthy and low yielding. The natural products Marinoquinoline A-F, Aplidiopsamine A and related natural products have very good antimalarial activity. Marinoquinoline A isolated from the gliding bacterium *Ohtaekwangia kribbensis* with Marinoquinoline B-F by Müller et al. in *Journal of Natural product*, 2011, 74, 603-608. Author mentioned that pyrroloquinoline shows weak antibacterial and antifungal activities. Whereas, Marinoquinoline A-F showed activity against *Plasmodium falciparum* K1 with $IC_{50}$ values ranging between 1.7 and 15 µM.

U.S. Pat. No. 9,518,051B2 assigned to Council Scientific & Industrial Research (CSIR) and granted on 13 Dec. 2016 discloses novel compounds with potential anti-malarial activity and process of synthesis thereof. Further, the process for the synthesis of known antimalarial natural products marinoquinazolinone A-F, aplidiopsamine A and their potential antimalarial analogues is disclosed.

The article titled 'Pd-Catalyzed Imine Cyclization: Synthesis of Antimalarial Natural Products Aplidiopsamine A, Marinoquinoline A, and Their Potential Hybrid NCLite-M1' by Santosh B. Mhaske* et. al published in the journal "*ORGANIC LETTERS* 2012 Vol. 14, No. 22 5804-5807" reports synthesis of antimalarial natural products. The article also reports new potential natural product hybrid NCLite-M1.

To date, drug resistance observed in only two species i.e. *Plasmodium falciparum, P. vivax*. Report also states that there is alarming rates of failure of dihydroartemisinin-piperaquine drug. Development of multi drug resistance strains of malaria parasite is great concern in controlling malaria worldwide. Transnational spreading of multidrug resistant is serious issue, hence there is need to find out novel antimalarial agent to combat the situation. In particular, there is urgent need to find out more effective drug to treat malaria as multi-drug resistance increasing worldwide. Accordingly, the present invention provides an antimalarial heterocyclic compounds of formula I or pharmaceutically acceptable salts thereof.

OBJECTS OF THE INVENTION

The main objective of the present invention is to provide an antimalarial heterocyclic compound of formula I, dimers or pharmaceutically acceptable salt thereof.

Another objective of the present invention is to provide a process for the preparation of heterocyclic compound of formula I, dimers or pharmaceutically acceptable salt thereof.

Still another objective of the present invention is to provide a pharmaceutical composition comprising the heterocyclic compounds of formula I, dimers or pharmaceutically acceptable salt thereof and at least one pharmaceutically acceptable excipient.

Yet another objective of the present invention is to provide a method for treating or preventing malarial infection in a subject in need thereof comprising administering a therapeutically effective amount of a heterocyclic compound of formula I, dimers or pharmaceutically acceptable salt thereof.

SUMMARY OF THE INVENTION

Accordingly, present invention provides a heterocyclic compound of Formula I, dimers or a pharmaceutically acceptable salts thereof

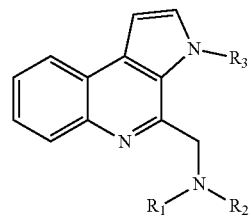

Formula I wherein
$R^1$ and $R^2$ may be same or different and each is independently selected from the group consisting of [C1-C50] alkyl, aryl, alkyl aryl, haloalkyl, hydroxy alkyl, alkoxy, hydroxy, halo, cyano, heteroalkyl, heteroaryl, alkyl heteroaryl, substituted or unsubstituted aryl/alkyl, alkenyl, alkenyl aryl, alkenyl heteroaryl, alkynyl, alkynyl aryl, alkynyl heteroaryl, cycloalkyl, heterocycloalkyl, alkyl cycloalkyl, alkyl heterocycloalkyl, alkyl carboxy, acyl, alkyl acyl, alkyl acyloxy, alkyl alkoxy, alkoxycarbonyl, alkyl alkoxycarbonyl, aminocarbonyl, alkyl aminocarbonyl, alkyl acylamino, alkyl ureido, amino, alkyl amino, sulfonyloxy, alkyl sulfonyloxy, sulfonyl, alkyl sulfonyl, sulfinyl, alkyl sulfinyl, alkyl sulfanyl, alkyl sulfonylamino;
$R^1$ and $R^2$ together may form a substituted or unsubstituted cyclic or heterocyclic aromatic ring;
$R^3$ is selected from hydrogen or phenyl sulfonyl ($-SO_2Ph$).

In an embodiment of the present invention, the heterocyclic compound is selected form the group comprising of:
a. N-ethyl-N-((3-(phenylsulfonyl)-3H-pyrrolo[2,3-c]quinolin-4-yl)methyl) ethanamine (Ia);
b. N-((3H-pyrrolo[2,3-c]quinolin-4-yl)methyl)-N-ethyl-ethanamine (Ib);
c. (((3-(phenylsulfonyl)-3H-pyrrolo[2,3-c]quinolin-4-yl)methyl)azanediyl) dimethanol (Ic);
d. (((3H-pyrrolo[2,3-c]quinolin-4-yl)methyl)azanediyl)dimethanol (Id);
e. N-methyl-N-((3-(phenylsulfonyl)-3H-pyrrolo[2,3-c]quinolin-4-yl)methyl)aniline (Ie);
f. N-((3H-pyrrolo[2,3-c]quinolin-4-yl)methyl)-N-methyl aniline (If);
g. 4-((3-(phenylsulfonyl)-3H-Pyrrolo[2,3-c]quinolin-4-yl)methyl)morpholine (Ig);
h. 4-((3H-pyrrolo[2,3-c]quinolin-4-yl)methyl)morpholine (Ih);
i. N,N-bis((3-(phenylsulfonyl)-3H-pyrrolo[2,3-c]quinolin-4-yl)methyl)aniline (Ii);
j. N,N-bis((3H-pyrrolo[2,3-c]quinolin-4-yl)methyl)aniline (Ij);
k. 4-methoxy-N-methyl-N-((3-(phenylsulfonyl)-3H-pyrrolo[2,3-c]quinolin-4-yl)methyl)aniline (Ik);
l. N-((3H-pyrrolo[2,3-c]quinolin-4-yl)methyl)-4-methoxy-N-methylaniline (Il) or
m. $N^4$-((3H-pyrrolo [2,3-c]quinolin-4-yl)methyl)-$N^1$,$N^1$-diethyl-$N^4$-methylpentane-1,4-diamine (Im).
n. 4-methyl-1H-pyrrolo[3,2-c]quinolone (In).

In another embodiment, present invention provides a process for the preparation of compound of Formula I, dimers or pharmaceutically acceptable salt thereof and the said process comprising the steps of:
i) charging [4-(bromomethyl)-3-(phenylsulfonyl)-3H-pyrrolo [2,3-c]quinoline of formula 1 and aliphatic amine in a solvent to obtain a reaction mixture;
ii) refluxing the reaction mixture as obtained in step (i) at a temperature in the range of 70-90° C. for period in the range of 10-14 hr to obtain a solution;
iii) charging [4-(bromomethyl)-3-(phenylsulfonyl)-3H-pyrrolo [2,3-c]quinoline of formula 1, base and aromatic amine in a solvent to obtain a reaction mixture;
iv) refluxing the reaction mixture as obtained in step (iii) at a temperature in the range of 70-90° C. for period in the range of 10-14 hr followed by cooling and diluting with water and extracting the reaction mass into solvent;
v) removing the solvent from the solution as obtained in step (ii) and (iv) under reduced pressure followed by purifying the crud product with flash silica gel column chromatography using an eluent to afford compound of formula I having —$SO_2Ph$ as $R_3$.
vi) charging the compound of formula I having —$SO_2Ph$ as $R_3$ as obtained in step
v) and base in a solvent to obtain a reaction mixture;
vii) refluxing the reaction mixture as obtained in step (vi) at a temperature in the range of 70-90° C. followed by removing the solvent under reduced pressure and dissolving the obtained residue in water and solvent;
viii) extracting aqueous layer with solvent followed by washing the combined organic layer with brine and drying over sodium sulfate;
ix) removing the solvent and purifying to obtain compound of formula I having —H as $R_3$.

In yet another embodiment of the present invention, said aliphatic amine is selected from the group comprising of diethylamine ($HNEt_2$), diethanolamine [$HN(CH_2CH_2OH)_2$] or $N^1$,$N^1$-diethylpentane-1,4-diamine.

In yet another embodiment of the present invention, said aromatic amine is selected from the group comprising of

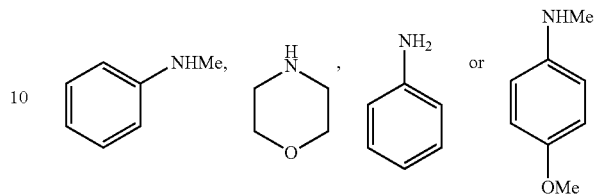

In yet another embodiment of the present invention, said solvent is selected from the group comprising of polar solvents, non-polar solvents, alcohol solvents, ether solvents, ester solvents, and the mixtures thereof.

In yet another embodiment of the present invention, polar solvents is selected from the group comprising of water, ammonia, sulfuric acid, deuterium oxide, ethanol, methanol, acetone, isopropanol, methyl ethyl ketone, n-propanol, acetonitrile, DMSO, DMF and mixtures thereof.

In yet another embodiment of the present invention, Nonpolar solvents is selected from the group comprising of chloroform, pentane, hexane, benzene, toluene, octane, decane, dimethyl ether, and dichloromethane, and mixtures thereof.

In yet another embodiment of the present invention, alcohol solvents is selected from the group comprising of methanol, ethanol, isopropanol, and mixtures thereof.

In yet another embodiment of the present invention, ether solvent is selected from the group comprising of tetrahydrofuran, diethyl ether, 1,4-dioxane, methyl tert-butyl ether, and mixtures thereof.

In yet another embodiment of the present invention, ester solvents is selected from the group comprising of methyl acetate, ethyl acetate, isopropyl acetate, tert-butyl acetate, and mixtures thereof.

In yet another embodiment of the present invention, said base is selected from the group comprising of sodium hydroxide, potassium hydroxide, sodium carbonate ($Na_2CO_3$) or potassium carbonate ($K_2CO_3$), sodium bicarbonate ($NaHCO_3$), potassium bicarbonate ($KHCO_3$).

In another embodiment, present invention provides a process for the preparation of heterocyclic compound, $N^4$-((3H-pyrrolo [2,3-c]quinolin-4-yl)methyl)-$N^1$,$N^1$-diethyl-$N^4$-methylpentane-1,4-diamine, of Formula (Im) and the said process comprising the steps of:
A) heating the reaction mixture of 4-methyl-3-(phenylsulfonyl)-3H-pyrrolo[2,3-c]quinoline of formula 2 and selenium dioxide ($SeO_2$) in a solvent at a temperature in the range of 60° C. to 80° C. for the period in the range of 10 to 14 hrs to afford 3-(phenylsulfonyl)-3H-Pyrrolo[2,3-c]quinoline-4-carbaldehyde of formula 3;

Formula 2

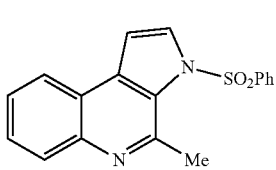

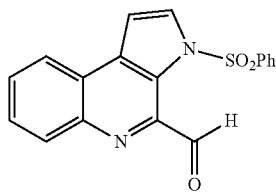

Formula 3

B) stirring the reaction mixture of step (a) and $N^1,N^1$-diethylpentane-1,4-diamine in presence of 4 Å molecular sieves in a solvent at temperature in the range of 25 to 30° C. for the period in the range of 20 to 24 hrs to afford crude imine of formula 4;

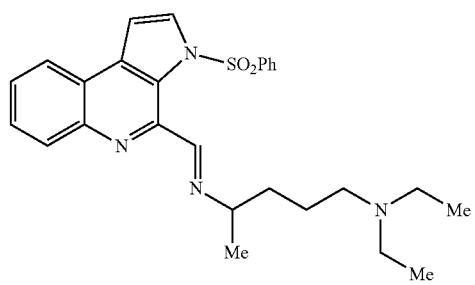

Formula 4

C) adding sodium borohydride to a cooled solution of crude imine of step (b) in a solvent followed by refluxing the reaction mixture at temperature in the range of 60 to 80° C. for the period in the range of 10 to 20 minutes to afford crude amine of formula 5;

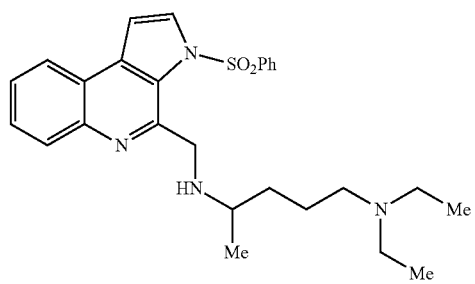

Formula 5

D) refluxing the reaction mixture of crude amine of step (c) in solvent and formaldehyde at temperature in the range of 60 to 80° C. for the period in the range of 20 minutes to 30 min followed by cooling reaction mixture at 0° C. and adding sodium borohydride (NaBH$_4$) at 0° C. and stirring the reaction mixture at a temperature in the range of 25 to 30° C. for the period in the range of 20 to 24 h to afford heterocyclic compound of formula (Im).

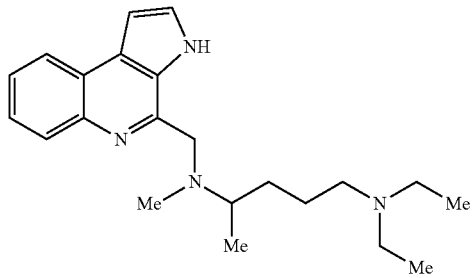

Formula Im

In yet another embodiment, present invention provides a pharmaceutical composition comprising a heterocyclic compound of Formula I, dimers, or pharmaceutically acceptable salt thereof, and a pharmaceutically acceptable carrier, diluent or excipient.

In yet another embodiment of the present invention, the said composition is useful as an antimalarial.

In yet another embodiment, present invention provides a method for the treating or preventing malarial infection in a subject in need thereof comprising administering a therapeutically effective amount of a compound formula I dimers, or pharmaceutically acceptable salt thereof.

Figure 2:
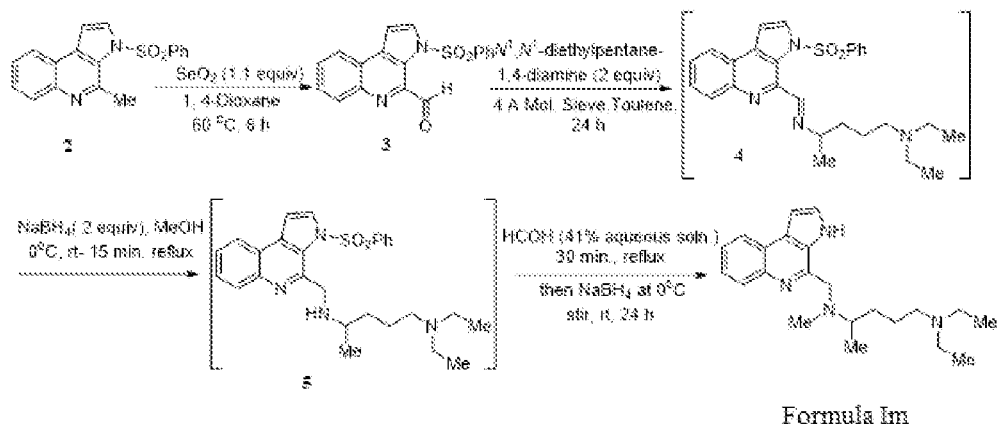

$R_1$ and $R_2$ together may form a substituted or unsubstituted cyclic or heterocyclic aromatic ring;

FIG. 2 represents the process steps for the preparation of heterocyclic compound of Formula (Im).

DETAILED DESCRIPTION OF THE INVENTION

The term "substituted" refers to one or more substituents selected from the group consisting of halogen, hydroxyl, nitro, cyano, thiocyanate, cyanamide, amido, thioamido, sulfonamide, $C_1$-$C_{50}$ alkyl, $C_2$-$C_{50}$ alkenyl, $C_2$-$C_{50}$ alkynyl, $C_3$-$C_{50}$ cycloalkyl, ester, thioester, dithioester, ether, thioether, $C_6$-$C_{18}$ aryl, heterocycle, peroxide, oxy derivative, thio derivative, acyl derivative, thioketone, sulfonyl derivative or sulfinyl derivative, thiol, nitrate, phosphate ester, thiophosphate ester, sulfate ester, carboxylic acid, phosphonic acid, phosphinic acid, sulfonic acid, amino, ammonium, imine, oxime, diazo, and hydroxamic acid.

The present invention provides an antimalarial heterocyclic compound of formula I, dimers or pharmaceutically acceptable salt thereof

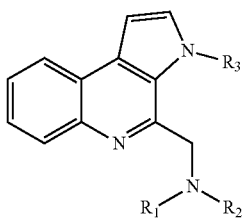

Formula I wherein,

R[1] and R[2] are same or different and each is independently selected from the group consisting of alkyl, aryl, alkyl aryl, haloalkyl, hydroxy alkyl, alkoxy, hydroxy, halo, cyano, heteroalkyl, heteroaryl, alkyl heteroaryl, substituted or unsubstituted aryl/alkyl, alkenyl, alkenyl aryl, alkenyl heteroaryl, alkynyl, alkynyl aryl, alkynyl heteroaryl, cycloalkyl, heterocycloalkyl, alkyl cycloalkyl, alkyl heterocycloalkyl, alkyl carboxy, acyl, alkyl acyl, alkyl acyloxy, alkyl alkoxy, alkoxycarbonyl, alkyl alkoxycarbonyl, aminocarbonyl, alkyl aminocarbonyl, alkyl acylamino, alkyl ureido, amino, alkyl amino, sulfonyloxy, alkyl sulfonyloxy, sulfonyl, alkyl sulfonyl, sulfinyl, alkyl sulfinyl, alkyl sulfanyl, alkyl sulfonylamino;

R[1] and R[2] together form a substituted or unsubstituted cyclic or heterocyclic aromatic ring;

R[3] is selected from the group consisting of hydrogen or phenyl sulfonyl (—SO$_2$Ph).

The compound of formula I is selected from group comprising of:
a. N-ethyl-N-((3-(phenylsulfonyl)-3H-pyrrolo [2,3-c]quinolin-4-yl)methyl)ethanamine [Ia];
b. N-((3H-pyrrolo[2,3-c]quinolin-4-yl)methyl)-N-ethylethanamine [Ib];
c. (((3-(phenylsulfonyl)-3H-pyrrolo[2,3-c]quinolin-4-yl)methyl)azanediyl)dimethanol [Ic];
d. (((3H-pyrrolo[2,3-c]quinolin-4-yl)methyl)azanediyl)dimethanol [Id];
e. N-methyl-N-((3-(phenylsulfonyl)-3H-pyrrolo[2,3-c]quinolin-4-yl)methyl)aniline [Ie];
f. N-((3H-pyrrolo[2,3-c]quinolin-4-yl)methyl)-N-methyl aniline [If];
g. 4-((3-(phenylsulfonyl)-3H-Pyrrolo[2,3-c]quinolin-4-yl)methyl)morpholine [Ig];
h. 4-((3H-pyrrolo[2,3-c]quinolin-4-yl)methyl)morpholine [Ih];
i. N,N-bis((3-(phenylsulfonyl)-3H-pyrrolo[2,3-c]quinolin-4-yl)methyl)aniline [Ii];
j. N,N-bis((3H-pyrrolo[2,3-c]quinolin-4-yl)methyl)aniline [Ij];
k. 4-methoxy-N-methyl-N-((3-(phenylsulfonyl)-3H-pyrrolo[2,3-c]quinolin-4-yl)methyl)aniline [Ik];
l. N-((3H-pyrrolo[2,3-c]quinolin-4-yl)methyl)-4-methoxy-N-methylaniline [Il] or
m. N$^4$-((3H-pyrrolo[2,3-c]quinolin-4-yl)methyl)-N$^1$,N$^1$-diethyl-N$^4$-methylpentane-1,4-diamine: [Im]

The present invention provides a process for the preparation of heterocyclic compound of formula I, dimers or pharmaceutically acceptable salt thereof and the said process comprising the step of:
i. reacting the 4-(bromomethyl)-3-(phenylsulfonyl)-3H-pyrrolo [2,3-c]quinoline of Formula 1 with aliphatic or aromatic amine to afford heterocyclic compound of formula I having —SO$_2$Ph as R$_3$;

ii. reacting the obtained compound of Formula I having —SO$_2$Ph as R$_3$ with a base to in a solvent to afford the heterocyclic compound of formula I having —H as R$_3$.

Figure 1:
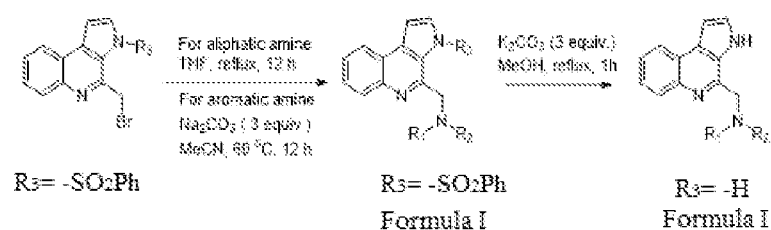
FIG. 1 represents a process for the preparation of compound of formula I, wherein $R_1$ and $R_2$ are same or different and each is independently selected from the group consisting of alkyl, aryl, alkyl aryl, haloalkyl, hydroxy alkyl, alkoxy, hydroxy, halo, cyano, heteroalkyl, heteroaryl, alkyl heteroaryl, substituted or unsubstituted aryl/alkyl, alkenyl, alkenyl aryl, alkenyl heteroaryl, alkynyl, alkynyl aryl, alkynyl heteroaryl, cycloalkyl, heterocycloalkyl, alkyl cycloalkyl, alkyl heterocycloalkyl, alkyl carboxy, acyl, alkyl acyl, alkyl acyloxy, alkyl alkoxy, alkoxycarbonyl, alkyl alkoxycarbonyl, aminocarbonyl, alkyl aminocarbonyl, alkyl acylamino, alkyl ureido, amino, alkyl amino, sulfonyloxy, alkyl sulfonyloxy, sulfonyl, alkyl sulfonyl, sulfinyl, alkyl sulfinyl, alkyl sulfanyl, alkyl sulfonylamino.

The process for the preparation of compound of formula I is depicted in FIG. 1.

The process for the preparation of heterocyclic compound of formula I, dimer or pharmaceutically acceptable salt thereof comprising the steps of:
i) charging [4-(bromomethyl)-3-(phenylsulfonyl)-3H-pyrrolo [2,3-c]quinoline of formula 1 and amine in a solvent;
ii) adding base when amine is aromatic amine;
iii) refluxing the reaction mixture at temperature in the range of 70-90° C. for period in the range of 10-14 hr to obtain a reaction mixture;
iv) cooling the reaction mixture as obtained in step (iii) followed by diluting the reaction mixture with water and extracting the reaction mass into solvent when amine is aromatic amine;
v) removing the solvent under reduced pressure;
vi) purifying the crud product with flash silica gel column chromatography using an eluent to afford compound of formula I having —SO$_2$Ph as R$_3$.

Optionally, process further comprise of removal of —SO$_2$Ph as R$_3$ to afford the heterocyclic compound of formula I having —H as R$_3$; wherein said process comprises of:
vii) charging the compound of formula I having —SO$_2$Ph as R$_3$ and base in a suitable solvent;
viii) refluxing the reaction mixture at a 70-90° C. for a period of 1 hr;
ix) removing the solvent under reduced pressure and dissolving the obtained residue in water and solvent;
x) extracting aqueous layer with solvent;
xi) washing the combined organic layer with brine and drying over sodium sulfate;
xii) removing the solvent under 200 mbar pressure at 50° C.; and
xiii) purifying the obtained crude product with flash silica gel column chromatography using an eluent (Pet. Ether/ethylacetate/DCM/Methanol) to afford compound of formula I having —H as R$_3$.

The solvent used at step (i) is selected from the group consisting of polar aprotic solvent, polar protic solvent, polar solvent, non-polar solvent or mixtures thereof.

Polar aprotic solvent is selected from the group consisting of N-methylpyrrolidone, tetrahydrofuran, ethyl acetate, acetone, dimethyl formamide, acetonitrile, dimethyl sulfoxide, propylene carbonate or mixtures thereof.

Polar protic solvent is selected from the group consisting of Formic acid, n-butanol, isopropanol, nitromethane, ethanol, methanol, acetic acid, water or mixtures thereof.

Polar aprotic solvent used instep (i) is more particularly dry tetrahydrofuran or acetonitrile. The aliphatic amine is selected from the group consisting of diethylamine (HNEt$_2$), diethanolamine [HN(CH$_2$CH$_2$OH)$_2$] or N$^1$,N$^1$-diethylpentane-1,4-diamine.

The aromatic amine is selected from the group consisting of aniline, N-methyl aniline, N-methyl p-anisidine, morpholine.

Base used is selected from the group consisting of sodium hydroxide, potassium hydroxide, sodium carbonate (Na$_2$CO$_3$) or potassium carbonate (K$_2$CO$_3$), sodium bicarbonate (NaHCO$_3$), potassium bicarbonate (KHCO$_3$), preferably sodium carbonate (Na$_2$CO$_3$) is used at step (ii) and potassium carbonate (K$_2$CO$_3$) is used at step (viii).

Temperature to conduct the reaction at step (ii), is in the range of 70° C. to 90° C., more particularly the temperature is 70° C. when dry tetrahydrofuran (THF) and 80° C. when acetonitrile is used.

Organic solvent used at steps (v) and (x) for extraction is selected from ester solvent, ketone solvent, non-polar solvent, or mixtures thereof, preferably ester solvents.

Ketone solvent used in selected from the group consisting of acetone, methyl propionone, ethyl propionone, n-butanone, methyl isobutyl ketone, and mixtures thereof.

Ester solvents used in selected from the group consisting of methyl acetate, ethyl acetate, isopropyl acetate, tert-butyl acetate, and mixtures thereof preferably ethyl acetate.

Non-polar solvents used in selected from the group consisting of chloroform, pentane, hexane, benzene, toluene, octane, decane, dimethyl ether, and dichloromethane, and mixtures thereof. Solvent used at step (viii) is selected from the group consisting of the polar solvents, non-polar solvents, alcohol solvents, ether solvents, ester solvents, amide solvents and the mixtures thereof.

Polar solvents is selected from the group consisting of water, ammonia, sulfuric acid, deuterium oxide, ethanol, methanol, acetone, isopropanol, methyl ethyl ketone, n-propanol, acetonitrile, DMSO, and DMF and mixtures thereof.

Non-polar solvents is selected from the group consisting of chloroform, pentane, hexane, benzene, toluene, octane, decane, dimethyl ether, and dichloromethane, and mixtures thereof. An alcohol solvent is selected from the group consisting of methanol, ethanol, isopropanol, and mixtures thereof. Ether solvents may include tetrahydrofuran, diethyl ether, 1,4-dioxane, methyl tert-butyl ether, and mixtures thereof.

Ester solvents is selected from the group consisting of methyl acetate, ethyl acetate, isopropyl acetate, tert-butyl acetate, and mixtures thereof.

In particularly useful embodiments, alcohol solvents are used and most preferably methanol is used as a solvent in step (viii).

Temperature to reflux the reaction mixture at step ix) is in the range of 65° C.-85° C., more preferably at 70° C.

Present invention provides a process for the synthesis of heterocyclic compound $N^4$-((3H-pyrrolo [2,3-c]quinolin-4-yl)methyl)-$N^1$,$N^1$-diethyl-$N^4$-methylpentane-1,4-diamine of Formula (Im) wherein $R_1$ or $R_2$ is heteroalkyl. The process is depicted in FIG. 2.

The process for the synthesis of heterocyclic compound $N^4$-((3H-pyrrolo [2,3-c]quinolin-4-yl)methyl)-$N^1$,$N^1$-diethyl-$N^4$-methylpentane-1,4-diamine of Formula (Im) wherein $R_1$ or $R_2$ is heteroalkyl comprises of the following steps:
a) heating the reaction mixture of 4-methyl-3-(phenylsulfonyl)-3H-pyrrolo[2,3-c]quinoline of formula 2 and selenium dioxide ($SeO_2$) in a solvent at a temperature in the range of 60° C. to 80° C. for the period in the range of 10 to 14 hrs to afford 3-(phenylsulfonyl)-3H-Pyrrolo[2,3-c]quinoline-4-carbaldehyde of formula 3;
b) stirring the reaction mixture of step (a) and $N^1$,$N^1$-diethylpentane-1,4-diamine in presence of 4 Å molecular sieves in a solvent at temperature in the range of 25 to 30° C. for the period in the range of 20 to 24 hrs to afford crude imine of formula 4;
c) adding sodium borohydride to a cooled solution of crude imine of step (b) in a solvent followed by refluxing the reaction mixture at temperature in the range of 60 to 80° C. for the period in the range of 10 to 20 minutes to afford crude amine of formula 5;
d) refluxing the reaction mixture of crude amine of step (c) in solvent and formaldehyde at temperature in the range of 60 to 80° C. for the period in the range of 20 minutes to 30 min followed by cooling reaction mixture at 0° C. and adding sodium borohydride ($NaBH_4$) at 0° C. and stirring the reaction mixture at room temperature in the range of 25 to 30° C. for the period in the range of 20 to 24 h to afford heterocyclic compound of formula (Im).

Suitable solvent used at steps a), b), c), and d) may include the polar solvents, non-polar solvents, alcohol solvents, ether solvents, ester solvents, amide solvents and the mixtures thereof. Polar solvents may include water, ammonia, sulfuric acid, deuterium oxide, ethanol, methanol, acetone, isopropanol, methyl ethyl ketone, n-propanol, acetonitrile, DMSO, and DMF and mixtures thereof. Non-polar solvents include chloroform, pentane, hexane, benzene, toluene, octane, decane, dimethyl ether, and dichloromethane, and mixtures thereof. Suitable alcohol solvents may include methanol, ethanol, isopropanol, and mixtures thereof. Suitable ether solvents include tetrahydrofuran, diethyl ether, 1,4-dioxane, methyl tert-butyl ether, and mixtures thereof. Suitable ester solvents include methyl acetate, ethyl acetate, isopropyl acetate, tert-butyl acetate, and mixtures thereof. In particularly useful embodiments, ether solvents are used at step a) and most preferably 1, 4-dioxane is used as a solvent at step a).

Non-polar solvents are used at step b) and most preferably toluene is used as a solvent at step b).

Alcohol solvents are used at step c) and d), and most preferably methanol is used as a solvent at step c) and d).

The present invention provides a pharmaceutical composition comprising a heterocyclic compound of formula I, dimers thereof or a stereoisomer, or ester or pharmaceutically acceptable salt thereof, and a pharmaceutically acceptable carrier, diluent or excipient.

The pharmaceutical compositions of the invention may be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, injections, gels and microspheres. The present invention relates to administering 'an effective amount' of the 'composition of invention' to the subject suffering from said disease. Accordingly, heterocyclic compound of formula I, dimers thereof and pharmaceutical compositions containing them may be administered using any amount, any form of pharmaceutical composition via any route of administration effective for treating the disease. Typical routes of administering such pharmaceutical compositions include, without limitation, oral, topical, transdermal, inhalation, parenteral, sublingual, buccal, rectal, vaginal, and intranasal.

Pharmaceutical compositions of the invention are formulated so as to allow the active ingredients contained therein to be bioavailable upon administration of the composition to a patient. Compositions that will be administered to a subject or patient may take the form of one or more dosage units. The dosage forms can also be prepared as sustained, controlled, modified and immediate dosage forms.

The present invention provides a method for the treating or preventing malarial infection in a subject in need thereof; comprising administering to the said subject a therapeutically effective amount of the heterocyclic compound of formula I, dimers thereof or a pharmaceutically acceptable salt thereof.

EXAMPLES

The following examples are given by way of illustration and therefore should not be construed to limit the scope of the invention.

Procedure A: Aliphatic Amines

Aliphatic amines

A

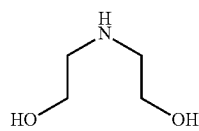

B

A dry single-neck round-bottom flask was charged with [4-(bromomethyl)-3-(phenylsulfonyl)-3H-pyrrolo [2,3-c] quinoline of formula 1 (0.25 mmol, 1 equiv.) and aliphatic amines of formula A or B (2.50 mmol, 10 equiv.). To this mixture, dry THF was added (4 mL) and reaction mixture was refluxed at 70° C. for 12 h. After completion of the reaction solvent was removed under reduced pressure and crude reaction mixture was purified using flash silica gel column chromatography using DCM/MeOH as eluents to obtain the pure compounds [1a] and [1c] of formula I respectively.

Procedure B: Aromatic Amines

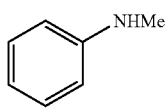

C

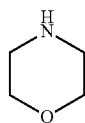

D

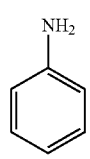

E

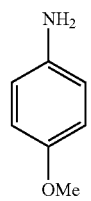

F

In a dry two-neck round-bottom flask containing 4-(bromomethyl)-3-(phenylsulfonyl)-3H-pyrrolo [2,3-c]quinoline of formula 1 (0.25 mmol, 1 equiv.), aromatic amine C—F (0.38 mmol, 1.5 equiv.) and Na$_2$CO$_3$ (1.25 mmol, 5 equiv.) were charged with dry acetonitrile (4 mL) via syringe. This mixture was refluxed at 80° C. for 12 h. After completion of reaction, it was cooled to room temperature (25° C.) and diluted with water (20 mL) and ethyl acetate (20 mL). Organic layer separated and aqueous layer was extracted with ethyl acetate (15 mL×2). Combined organic layer was washed with brine (10 mL×2) and dried over sodium sulphate. Solvent was removed under reduced pressure and crude product was purified using flash silica gel column chromatography using petroleum ether/EtOAc as eluents to obtain the desired compounds [Ie], [Ig], [Ii] and [Ik] of Formula I respectively.

Procedure C: For —SO$_2$Ph Deprotection

A dry single-neck round-bottom flask charged with compound of Formula I (Ia, Ic, Ie, Ig, Ii, Ik,) (0.12 mmol, 1 equiv.), K$_2$CO$_3$ (0.36 mmol, 3 equiv.) and methanol (5 mL) and this mixture was refluxed at 70° C. for 1 h. After completion of reaction solvent was removed under reduced pressure and residue was dissolved in water (10 mL) and ethyl acetate (10 mL). Organic layer separated and aqueous layer washed with ethyl acetate (10 mL×2). Combined organic layer were washed with brine (10 mL) and dried over sodium sulphate. Solvent was removed under reduced pressure and crude product was purified using flash silica gel column chromatography using suitable eluents to furnish desired compounds [Ib], [Id], [If], [Ih] [Ij] and [Il] of Formula I respectively.

Example 1

N-ethyl-N-((3-(phenylsulfonyl)-3H-pyrrolo [2,3-c] quinolin-4-yl)methyl)ethanamine [Ia]

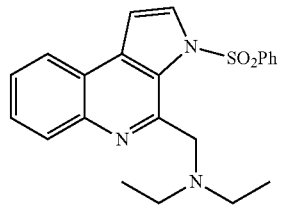

Following general experimental procedure A, [1a] is obtained as brown oil (76 mg, 77%); R$_f$=0.5 (19:1 DCM/MeOH); $^1$H NMR (400 MHz, CDCl$_3$): δ 1.24 (t, J=7.2 Hz, 6H), 3.42 (q, J=7.1 Hz, 4H), 4.78 (s, 2H), 7.32 (d, J=3.6 Hz, 1H), 7.56 (t, J=7.3 Hz, 2H), 7.64 (dd, J=7.3 Hz, 2H), 7.71 (t, J=7.3 Hz, 1H), 7.80 (d, J=7.9 Hz, 2H), 8.05 (d, J=3.6 Hz, 1H), 8.14 (d, J=7.9 Hz, 1H), 8.28 (d, J=7.9 Hz, 1H); $^{13}$C NMR (100 MHz, CDCl$_3$): δ9.6, 48.8, 53.6, 106.8, 121.9, 122.8, 126.1, 126.6, 127.8, 128.9, 129.3 129.6, 130.2, 132.3, 134.8, 136.2, 138.1, 142.3; HRMS (ESI–TOF) (m/z): [M+H]$^+$ Calcd for C$_{22}$H$_{24}$N$_3$O$_2$S 394.1584. Found 394.1582.

Example 2

N-((3H-pyrrolo[2,3-c]quinolin-4-yl)methyl)-N-ethylethanamine [Ib]

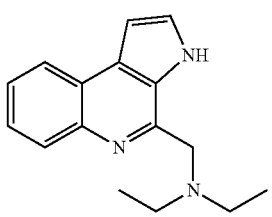 [SMILES: CCN(CC)Cc1nc2ccccc2c2cc[nH]c12]

Following general experimental procedure C, [1b] obtained as brown oil (26 mg, 87%); $R_f$=0.6 (9:1 DCM/MeOH); $^1$H NMR (400 MHz, CDCl$_3$): δ 1.15 (t, J=7.3 Hz, 6H), 2.71 (q, J=7.3 Hz, 4H), 4.24 (s, 2H), 7.04 (d, J=2.4 Hz, 1H), 7.42 (d, J=3.1 Hz, 1H), 7.52-7.61 (m, 2H), 8.11 (d, J=7.3 Hz, 1H), 8.20 (d, J=8.6 Hz, 1H), 10.90 (bs, 1H); $^{13}$C NMR (100 MHz, CDCl$_3$): δ 11.8, 47.7, 60.6, 100.9, 122.8, 123.4, 125.2, 125.4, 125.8, 128.4, 128.8, 129.0, 142.4, 147.3; HRMS (ES-TOF) (m/z):[M+H]$^+$ Calcd for C$_{16}$H$_{20}$N$_3$ 254.1650. Found 254.1652.

Example 3

(((3-(phenylsulfonyl)-3H-pyrrolo[2,3-c]quinolin-4-yl)methyl)azanediyl)dimethanol [Ic]

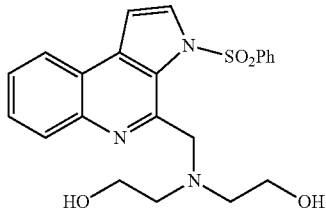

Following general experimental procedure A, [1c] obtained as pale yellow solid (42 mg, 40%); $R_f$=0.3 (9:1 DCM/MeOH); Mp=98-99° C.; $^1$H NMR (400 MHz, CDCl$_3$): δ 2.86 (t, J=4.8 Hz, 4H), 3.40 (t, J=4.8 Hz, 4H), 4.37 (s, 2H), 4.95 (bs, 2H), 7.31 (d, J=3.6 Hz, 1H), 7.50 (t, J=7.9 Hz, 2H), 7.62 (dd, J=7.3 Hz, 2H), 7.68 (d, J=7.9 Hz, 3H), 8.07-8.15 (m, 3H); $^{13}$C NMR (100 MHz, CDCl$_3$): δ58.6, 59.1, 59.9, 106.4, 121.9, 122.9, 126.3, 126.9, 127.1, 128.3, 128.9, 129.8, 132.8, 134.4, 136.0, 139.1, 142.7, 148.9; HRMS (ESI-TOF) (m/z):[M+H]$^+$ Calcd for C$_{22}$H$_{24}$N$_3$O$_4$S 426.1482. Found 426.1480.

Example 4

(((3H-pyrrolo[2,3-c]quinolin-4-yl)methyl)azanediyl)dimethanol [Id]

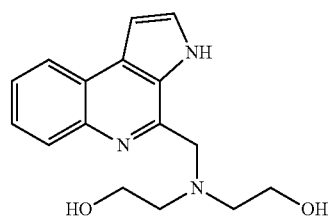 [SMILES: OCCN(CCO)Cc1nc2ccccc2c2cc[nH]c12]

Following general experimental procedure C, [1d] obtained as brown sticky solid (25 mg, 74%); $R_f$=0.5 (4:1 DCM/MeOH); $^1$H NMR (500 MHz, MeOD$_4$): δ 2.88 (t, J=5.8 Hz, 4H), 3.72 (t, J=5.7 Hz, 4H), 4.34 (s, 2H), 7.13 (d, J=3.1 Hz, 1H), 7.60 (dd, J=4.6 Hz, 2H) 7.62 (d, J=2.6 Hz, 1H), 8.06 (dd, J=5.3 Hz, 1H), 8.28 (dd, J=4.2 Hz, 1H); $^{13}$C NMR (125 MHz, MeOD$_4$): δ 58.2, 60.3, 60.6, 101.7, 124.2, 124.9, 126.9, 127.1, 128.2, 129.0, 129.2, 130.8, 142.1, 149.4; HRMS (ESI-TOF) (m/z):[M+H]$^+$ Calcd for C$_{16}$H$_{20}$N$_3$O$_2$ 286.1550. Found 286.1552.

Example 5

N-methyl-N-((3-(phenylsulfonyl)-3H-pyrrolo[2,3-c]quinolin-4-yl)methyl)aniline [Ie]

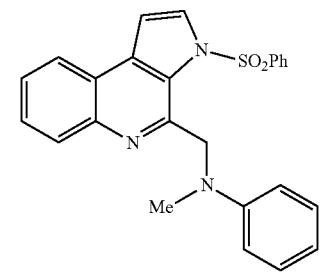

Following general experimental procedure B, [1e] obtained as white solid (40 mg, 38%); $R_f$=0.6 (4:1 Petroleum ether/EtOAc); Mp=146-148° C.; $^1$H NMR (400 MHz, CDCl$_3$): δ 3.16 (s, 3H), 5.08 (s, 2H), 6.36 (d, J=8.5 Hz, 2H), 6.56 (t, J=7.3 Hz, 1H), 7.01 (t, J=7.9 Hz, 2H), 7.31 (d, J=3.1 Hz, 1H), 7.47-7.60 (m, 4H), 7.64 (t, J=7.3 Hz, 1H), 7.72 (d, J=7.9 Hz, 2H), 7.92 (d, J=7.3 Hz, 1H), 8.06-8.13 (m, 2H); $^{13}$C NMR (100 MHz, CDCl$_3$): δ39.9, 56.8, 106.2, 111.9, 115.6, 121.7, 122.6, 126.4, 126.5, 127.5, 127.8, 128.7, 129.8, 129.9, 131.6, 134.2, 135.1, 139.3, 143.3, 146.0, 149.8; HRMS (ESI-TOF) (m/z):):[M+H]$^+$ Calcd for C$_{25}$H$_{22}$N$_3$O$_2$S 428.1427. Found 428.1421.

Example 6

N-((3H-pyrrolo[2,3-c]quinolin-4-yl)methyl)-N-methyl aniline [1f]

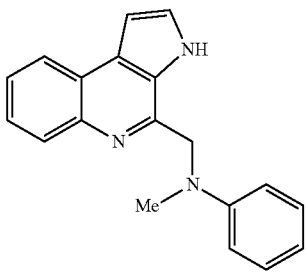 [SMILES: CN(Cc1nc2ccccc2c2cc[nH]c12)c1ccccc1]

Following general experimental procedure C, [1f] obtained as white solid (32 mg, 94%); $R_f$=0.6 (7:3 Petroleum ether/EtOAc); Mp=139-141° C.; $^1$H NMR (400 MHz, CDCl$_3$): δ 2.99 (s, 3H), 4.99 (s, 2H), 6.92 (t, J=7.3 Hz, 1H), 7.01-7.12 (m, 3H), 7.29-7.40 (m, 3H), 7.56-7.69 (m, 2H), 8.16 (d, J=7.9 Hz, 1H), 8.22 (d, J=7.9 Hz, 1H), 9.46 (bs, 1H); $^{13}$C NMR (100 MHz, CDCl$_3$): δ39.2, 60.8, 101.3, 114.9, 119.4, 122.9, 123.4, 125.7, 125.9, 126.1, 127.8, 129.0, 129.2, 129.7, 142.4, 146.7, 150.5; HRMS (ESI-TOF) (m/z): [M+H]$^+$ Calcd for C$_{19}$H$_{18}$N$_3$ 288.1495; Found 288.1491.

Example 7

4-((3-(phenylsulfonyl)-3H-Pyrrolo[2,3-c]quinolin-4-yl)methyl)morpholine [1g]

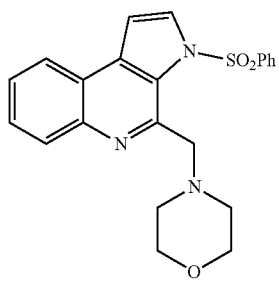

Following general experimental procedure B, [1g] obtained as White solid (43 mg, 43%); $R_f$=0.3 (1:1 Petroleum ether/EtOAc); Mp=138-140° C.; $^1$H NMR (500 MHz, CDCl$_3$): δ 2.56 (s, 4H), 3.60 (s, 4H), 4.28 (s, 2H), 7.28 (s, 1H), 7.46 (t, J=8.0 Hz, 2H), 7.55-7.64 (m, 2H), 7.69 (t, J=8.0 Hz, 1H), 7.81 (d, J=7.6 Hz, 2H), 7.99 (d, J=3.4 Hz, 1H), 8.13 (d, J=8.0 Hz, 1H), 8.17 (d, J=8.4 Hz, 1H); $^{13}$C NMR (125 MHz, CDCl$_3$): δ53.7, 63.7, 66.8, 106.7, 121.8, 122.8, 126.4, 126.7, 128.1, 128.6, 129.4, 129.5, 132.6, 133.9, 135.6, 139.6, 143.0, 146.1; HRMS (ESI-TOF) (m/z):):[M+H]$^+$ Calcd for C$_{22}$H$_{22}$N$_3$O$_3$S 408.1376. Found 408.1372.

Example 8

4-((3H-pyrrolo[2,3-c]quinolin-4-yl)methyl)morpholine [1h]

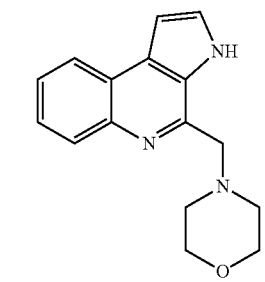 [SMILES: c1ccc2c(c1)nc(CN1CCOCC1)c1[nH]ccc12]

Following general experimental procedure C, [1h] obtained as White solid (28 mg, 88%); $R_f$=0.3 (9:1 DCM/MeOH); Mp=148-150° C.; $^1$H NMR (400 MHz, CDCl$_3$): δ 2.64 (s, 4H), 3.80 (s, 4H), 4.17 (s, 2H), 7.06 (d, J=1.8 Hz, 1H), 7.44 (d, J=1.8 Hz, 1H), 7.53-7.62 (m, 2H), 8.12 (d, J=7.9 Hz, 1H), 8.20 (d, J=7.3 Hz, 1H), 10.49 (bs, 1H); $^{13}$C NMR (100 MHz, CDCl$_3$): δ54.0, 65.4, 67.1, 101.3, 122.8, 123.4, 125.4, 125.7, 126.0, 128.3, 128.5, 129.1, 142.4, 145.5; HRMS (ESI-TOF) (m/z):):[M+H]$^+$ Calcd for C$_{16}$H$_{18}$N$_3$O 268.1444. Found 268.1442.

Example 9

N,N-bis((3-(phenylsulfonyl)-3H-pyrrolo[2,3-c]quinolin-4-yl)methyl)aniline [1i]

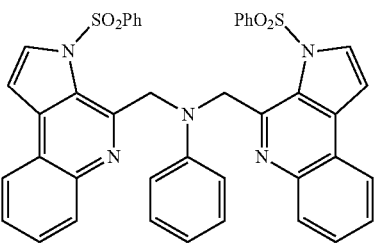

Following general experimental procedure B, [1i] obtained as Brown solid (45 mg, 25%); $R_f$=0.3 (3:2 Petroleum ether/EtOAc); Mp=188-190° C.; $^1$H NMR (400 MHz, CDCl$_3$): δ 5.21 (s, 4H), 6.29 (d, J=7.9 Hz, 2H), 6.51 (t, J=7.3 Hz, 1H), 6.90 (t, J=7.9 Hz, 2H), 7.03 (t, J=7.9 Hz, 4H), 7.24 (t, J=7.3 Hz, 2H), 7.31 (d, J=3.6 Hz, 2H), 7.55-7.65 (m, 6H), 7.68 (t, J=7.3 Hz, 2H), 8.07 (d, J=3.6 Hz, 2H), 8.15 (t, J=7.9 Hz, 4H); $^{13}$C NMR (100 MHz, CDCl$_{13}$): δ55.8, 105.7, 112.1, 115.4, 121.9, 122.7, 126.4, 127.4, 127.8, 128.4, 129.3, 130.1, 131.4, 133.8, 134.8, 139.0, 143.5, 146.5, 150.4, 157.6; HRMS (ESI-TOF) (m/z):):[M+H]$^+$ Calcd for C$_{42}$H$_{32}$N$_5$O$_4$S$_2$ 734.1890. Found 734.1876.

Example 10

N,N-bis((3H-pyrrolo[2,3-c]quinolin-4-yl)methyl)aniline [Ij]

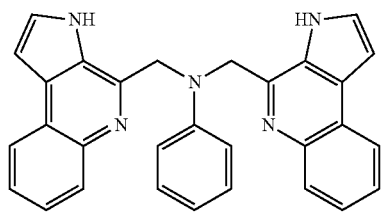 [SMILES: c1ccc(N(Cc2nc3ccccc3c3cc[nH]c23)Cc2nc3ccccc3c3cc[nH]c23)cc1]

Following general experimental procedure C, [1j] obtained as Brown solid (30 mg, 55%); $R_f$=0.3 (3:7 Petroleum ether/EtOAc); Mp=242-244° C.; $^1$H NMR (400 MHz, DMSO-d$_6$): δ 5.36 (s, 4H), 6.59 (t, J=7.3 Hz, 1H), 6.71 (d, J=8.5 Hz, 2H), 6.95 (t, J=7.3 Hz, 2H), 7.25 (s, 2H), 7.56-7.67 (m, 4H), 7.89 (s, 2H), 8.18 (d, J=7.9 Hz, 2H), 8.34 (d, J=7.9 Hz, 2H), 13.35 (bs, 2H); $^{13}$C NMR (100 MHz, DMSO-d$_6$): δ60.2, 101.3, 114.9, 118.5, 123.4, 123.5, 125.7, 126.1, 126.9, 128.1, 128.4, 128.6, 128.8, 141.6, 148.2, 150.9; HRMS (ESI–TOF) (m/z):[M+H]$^+$ Calcd for $C_{30}H_{24}N_5$ 454.2026. Found 454.2020.

Example 11

4-methoxy-N-methyl-N-((3-(phenylsulfonyl)-3H-pyrrolo[2,3-c]quinolin-4-yl)methyl)aniline [Ik]

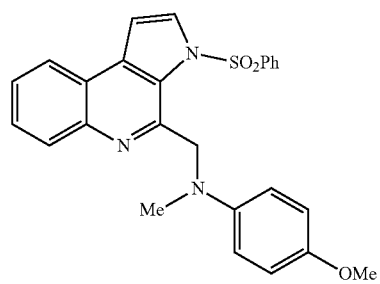

Following general experimental procedure B, [1k] obtained as yellow solid (52 mg, 45%); $R_f$=0.8 (4:1 Petroleum ether/EtOAc); Mp=48-50° C.; $^1$H NMR (400 MHz, CDCl$_3$): δ 3.05 (s, 3H), 3.70 (s, 3H), 5.03 (s, 2H), 6.39 (d, J=9.2 Hz, 2H), 6.64 (d, J=9.2 Hz, 2H), 7.30 (d, J=3.7 Hz, 1H), 7.45-7.65 (m, 5H), 7.70 (d, J=7.3 Hz, 2H), 7.95 (d, J=7.3 Hz, 1H), 8.05-8.13 (m, 2H); $^{13}$C NMR (100 MHz, CDCl$_3$): δ40.3, 55.7, 57.6, 106.1, 113.7, 114.3, 121.7, 122.6, 126.3, 126.5, 127.6, 127.8, 129.7, 129.8, 131.7, 134.1, 135.1, 139.3, 143.3, 144.7, 146.5, 151.0; HRMS (ESI–TOF) (m/z):):[M+H]$^+$ Calcd for $C_{26}H_{24}N_3O_3S$ 458.1533. Found 458.1524.

Example 12

N-((3H-pyrrolo[2,3-c]quinolin-4-yl)methyl)-4-methoxy-N-methylaniline [Il]

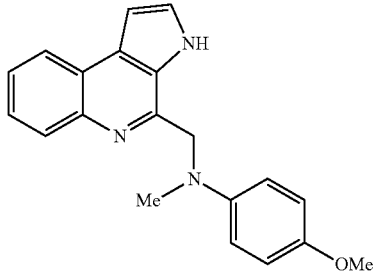 [SMILES: COc1ccc(N(C)Cc2nc3ccccc3c3cc[nH]c23)cc1]

Following general experimental procedure C, [1l] obtained as Brown oil (27 mg, 71%); $R_f$=0.5 (7:1 Petroleum ether/EtOAc); $^1$H NMR (400 MHz, CDCl$_3$): δ 2.92 (s, 3H), 3.79 (s, 3H), 4.86 (s, 2H), 6.89 (d, J=8.5 Hz, 2H), 7.00-7.10 (m, 3H), 7.34 (s, 1H), 7.55-7.64 (m, 2H), 8.15 (d, J=7.9 Hz, 1H), 8.21 (d, J=7.3 Hz, 1H), 9.81 (bs, 1H); $^{13}$C NMR (100 MHz, CDCl$_3$): δ40.9, 55.6, 62.3, 101.2, 114.9, 117.7, 122.9, 123.4, 125.7, 125.8, 126.1, 128.0, 128.9, 129.0, 142.4, 145.2, 146.8, 153.8; HRMS (ESI–TOF) (m/z):):[M+H]$^+$ Calcd for $C_{20}H_{20}N_3O$ 318.1601. Found 318.1596.

Example 13

$N^4$-((3H-pyrrolo[2,3-c]quinolin-4-yl)methyl)-$N^1$,$N^1$-diethyl-$N^4$-methylpentane-1,4-diamine of Formula (Im)

Formula (Im)

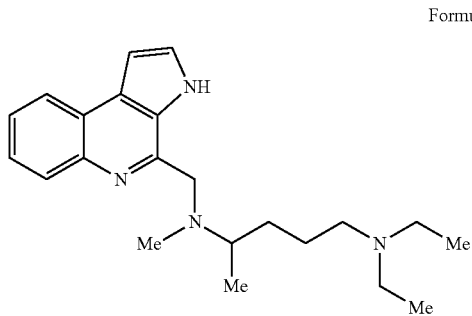

a) 3-(phenylsulfonyl)-3H-Pyrrolo[2,3-c]quinoline-4-carbaldehyde (3)

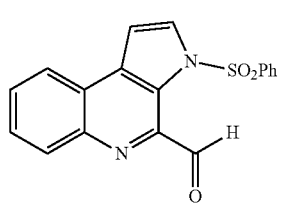

A dry single-neck round-bottom flask was charged with 4-methyl-3-(phenylsulfonyl)-3H-pyrrolo[2,3-c]quinolone of formula 2 (500 mg, 1.55 mmol) and SeO$_2$ (188 mg, 1.70 mmol) under argon atmosphere. 1, 4-dioxane (5 mL) was added via syringe and reaction mixture heated at 60° C. for 12 h under argon atmosphere. After this time, solvent was removed under reduced pressure and crude reaction mixture was diluted with ethyl acetate (20 mL) and water (20 mL). Then, organic layer was separated and aqueous layer extracted with ethyl acetate (20 mL×2). Combined organic layer was washed using brine (20 mL) and dried over sodium sulphate. Evaporation of solvent provided crude product, which was purified using flash silica gel column chromatography (9:1 Petroleum ether/EtOAc) to obtained desired aldehyde as pale yellow solid (410 mg, 78%).

R$_f$=0.5 (4:1 Petroleum ether/EtOAc); Mp=173-175° C.; $^1$H NMR (500 MHz, CDCl$_3$): δ 7.34 (d, J=3.6 Hz, 1H), 7.51 (t, J=7.3 Hz, 2H), 7.62 (t, J=7.3 Hz, 1H), 7.69-7.80 (m, 2H), 7.86 (d, J=7.9 Hz, 2H), 8.00 (d, J=3.6 Hz, 1H), 8.18 (d, J=7.9 Hz, 1H), 8.31 (d, J=8.5 Hz, 1H), 10.55 (s, 1H); $^{13}$C NMR (125 MHz, CDCl$_3$): δ 107.5, 123.1, 123.5, 125.4, 126.9, 128.9, 129.3, 130.7, 132.1, 134.3, 135.9, 138.1, 143.0, 143.2, 190.2; HRMS (ESI–TOF) (m/z):):[M+Na]$^+$ Calcd for C$_{18}$H$_{12}$N$_2$O$_3$SNa 359.0461. Found 359.0455.

b) N$^4$-((3H-pyrrolo [2,3-c]quinolin-4-yl)methyl)-N$^1$, N$^1$-diethyl-N$^4$-methylpentane-1,4-diamine In a flame dried single-neck round-bottom flask containing 10-20 freshly activated molecular sieves (4 Å) and 3-(phenylsulfonyl)-3H-Pyrrolo[2,3-c]quinoline-4-carbaldehyde (3, 100 mg, 0.29 mmol) was added dry toluene (2-3 mL) via syringe. N$^1$,N$^1$-diethylpentane-1,4-diamine (117 μL, 0.59 mmol) was added and mixture was stirred at 28° C. for 24 h. After this time, reaction mixture was filtered over celite and celite layer washed with ethyl acetate (10 mL×2). Combined filtrate was concentrated under reduced pressure and obtained crude imine (4), which was used as it is for further transformation.

Crude imine of formula 4 (140 mg, 0.29 mmol) dissolved in methanol (4 mL) was cooled at 0° C. and NaBH$_4$ (33 mg, 0.88 mmol) was added. Then, reaction mixture was warmed to 28° C. and then refluxed at 70° C. for 15 minutes. Water (20 mL) was added in mixture and it was extracted with EtOAc (15 mL×2). Organic layer washed with brine (10 mL) and dried over sodium sulphate. Solvent was removed under reduced pressure and crude amine (5) used for further reaction.

Crude amine of formula 5 (100 mg, 0.21 mmol) was dissolved in methanol (2 mL) and it was treated with formaldehyde (41% aqueous solution, 75 μL, 1.04 mmol). The solution was heated under at 70° C. for 30 min, after cooling in ice bath NaBH$_4$ (28 mg, 0.83 mmol) was added in small portions, and this mixture was stirred at 28° C. for 24 h. Solvent was evaporated under reduced pressure and residue was dissolved in DCM and saturated ammonium chloride solution. Organic layer was separated and aqueous layer extracted with DCM (20 mL×2). Combined organic layer was washed with brine (20 mL) and dried over sodium sulphate. The crude product was subjected to flash silica gel column chromatography using NH$_4$OH:MeOH:DCM (2:2: 96 to 2:4:94) v/v to obtain compound of Formula (Im) as yellow oil (25 mg, 34%).

R$_f$=0.5 (4:1 DCM/MeOH); $^1$H NMR (400 MHz, CDCl$_3$): δ 1.04 (t, J=7.3 Hz, 6H), 1.14 (d, J=6.1 Hz, 3H), 1.38-1.50 (m, 1H), 1.55-1.64 (m, 2H), 1.65-1.76 (m, 1H), 2.26 (s, 3H), 2.42-2.51 (m, 2H), 2.56 (q, J=6.7 Hz, 4H), 2.85-2.97 (m, 1H), 4.22 (q, J=14.6 Hz, 2H), 7.03 (d, J=3.1 Hz, 1H), 7.41 (d, J=2.4 Hz, 1H), 7.50-7.60 (m, 2H), 8.11 (d, J=7.9 Hz, 1H), 8.20 (d, J=7.9 Hz, 1H), 10.71 (bs, 1H); $^{13}$C NMR (100 MHz, CDCl$_3$): δ11.5, 13.4, 24.9, 31.8, 36.6, 46.8, 52.9, 58.7, 60.8, 100.9, 122.8, 123.4, 125.3, 125.4, 125.8, 128.4, 128.5, 129.0, 142.4, 147.5; HRMS (ESI–TOF) (m/z):):[M+H]$^+$ Calcd for C$_{22}$H$_{33}$N$_4$ 353.2700. Found 353.2694.

Example 13

4-methyl-1H-pyrrolo[3,2-c]quinoline Compound of Formula [In]

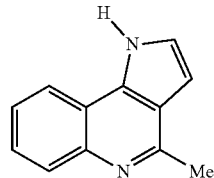

Following general experimental procedure C, Formula In obtained as White solid (19 mg, 86%); R$_f$=0.2 (1:1 Petroleum ether/EtOAc); Mp=233-235° C.; $^1$H NMR (400 MHz, Acetone-d$_6$): δ 2.86 (s, 3H), 7.15 (d, J=3.1 Hz, 1H), 7.48-7.56 (m, 2H), 7.61 (d, J=3.1 Hz, 1H), 8.03 (d, J=7.3 Hz, 1H), 8.25 (dd, J=2.4, 7.9 Hz, 1H); $^{13}$C NMR (100 MHz, Acetone-d$_6$): δ21.2, 101.9, 123.7. 124.1, 125.6, 126.0, 127.1, 128.3, 129.7, 143.7, 146.8; HRMS (ESI–TOF) (m/z):):[M+H]$^+$ Calcd for C$_{12}$H$_{11}$N$_2$ 183.0917. Found 183.0916.

Example 15

Antimalarial Activity Methods

*Plasmodium* Culture

*Plasmodium falciparum* 3D7 strain from Malaria Research and Reference Reagent Resource Center (ID NO: MRA-102). *Plasmodium falciparum* (3D7) is cultured in the laboratory as per standard protocols [AzarRadfar, Darío Méndez, Carlos Moneriz, María Linares, Patricia Marín-García, Antonio Puyet, AmaliaDiez & José M Bautista. Synchronous culture of *Plasmodium falciparum* at high parasitemia levels Nature Protocols 2009, 4, 1899-1915]. When the parasitemia (i.e., percent infection of human RBCs) reaches >15%, 1 mL of culture suspension is layered over 10 mL of 60% percoll (pH and osmolality adjusted using PBS) and centrifuged at 3000 rpm for 5 min using a swing out rotor. This separates late stage parasite (trophozoite and schizont) infected RBC (as a band on top of the percoll cushion) from early stage parasite (ring) infected and uninfected RBCs (as pellet at the bottom of the percoll cushion). The >90% enriched late stage parasite infected RBCs are collected, washed with complete RPMI media and added to a 2% hematocrit RBC suspension such that the final parasitemia is around 2%. The parasites grow in a synchronous manner for at least 2 rounds of asexual cycle (48 hours). This culture is then used for anti-malarial screening as given below.

Anti-Malarial Screen

200 μL of ring stage parasite culture at ~2% parasitemia (see above) is added to each well in a 96 well plate pre-seeded with the compound of interest at the required concentration. 1 mM and 10 mM stocks dilutions of the compounds are prepared in cell culture grade DMSO, and the final concentration used in the assay is either 10 μM (for identifying molecules affecting parasite growth) or a serial dilution from 10 µM to 1 nM (for estimating the dose response and $EC_{50}$ value). All compounds are plated in triplicates as biological replicates. Each 96 well plate also includes negative control (compound untreated & DMSO only treated culture) and positive control (standard anti-malarial compounds treated culture). Standard anti-malarials used are chloroquine, artemisinine and atovaquone, each at 1 µM concentration although their respective $IC_{50}$s are >20 nM for the 3D7 strain of *P. falciparum*. After plating, the culture is incubated in standard growth condition for 60 hours, after which the cultures are processed for testing the effect of compounds on parasite growth as given below.

Estimating Parasite Growth by SybrGreen Staining

The inventors have standardized a SybrGreen dye based staining protocol for estimating parasite growth, which is a modification of previously published protocol [Plouffe et. al, 2008]. SybrGreen dye binds to DNA and only the DNA bound dye gives a specific fluorescence emission (520 nM) when excited (498 nM). Since only the parasites have DNA (as human RBCs are devoid of nucleus), the SybrGreensignal is a direct indictor of parasite growth. A standard fluorescent plate reader issued for assay read out, and the staining is done as follows. 25 µL of 10× stock containing of dye and Triton X100 (0.5%) is added to each of 200 µL culture growing in a 96 well plate and mixed well and incubated for 15 min-30 min before reading fluorescence emission using the plate reader at the appropriate wavelength.

Data from Anti-Malarial Screening

The table below provides the results from the anti-malarial screening experiment. First the growth inhibition assay was carried out in which the molecules were tested against the parasite at 10 µM concentration. ≥80% growth inhibition was seen in case of all molecules, except compound of formula Ie & NCLite-M1. So the dose response was carried out for all molecules and the EC50 values are given.

| Molecule Name | Average % growth Inhibition | Stdev | EC50 (µM) | stdev |
| --- | --- | --- | --- | --- |
| Ia | 99.74 | 0.16 | 0.27 | 0.02 |
| Ib | 97.00 | 0.51 | 8.58 | 1.38 |
| Ic | 93.56 | 0.89 | >10 | n/a |
| Id | 91.52 | 0.98 | 4.48 | 0.40 |
| Ie | 55.53 | 2.21 | >10 | n/a |
| If | 89.92 | 0.59 | 8.72 | 2.55 |
| Ig | 79.38 | 3.44 | 7.86 | 0.63 |
| Ih | 86.85 | 2.85 | 1.99 | 0.00 |
| Ii | 88.29 | 2.37 | >10 | n/a |
| Ij | 84.06 | 3.40 | >10 | n/a |
| Ik | 90.22 | 0.19 | >10 | n/a |
| Il | 94.07 | 0.67 | 0.74 | 0.01 |
| Im | 98.47 | 0.17 | 0.17 | 0.04 |
| Compound of formula 3 | 88.34 | 2.54 | >10 | n/a |
| In | 99.13 | 0.08 | 3.70 | 0.64 |
| NCLite-M1 | 9.18 | 3.18 | ND | ND |

NCLite-M1 = (3-((3H)-pyrrolo[2,3-c]quinoline-4-yl)methyl)quinazolin-4(3H)-one).

NCLite-M1=(3-((3H)-pyrrolo[2,3-c]quinoline-4-yl) methyl)quinazolin-4(3H)-one.

ADVANTAGES OF THE INVENTION

1. New heterocyclic compound of formula I is disclosed which are used for the treatment of malarial infection.
2. Simple and cost-effective process for the preparation of compound of formula I.
3. These compounds due to their unique aromatic and multifunctional amine groups may be very good G-quadruplex binding agents, which is a requirement for anticancer drugs.

The invention claimed is:
1. A compound of Formula I:

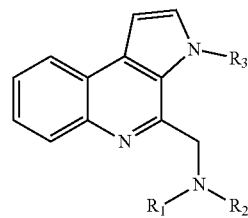

Formula I or a pharmaceutically acceptable salt or stereoisomer thereof,
wherein:
$R_1$ is $C_1$-$C_{10}$ alkyl or $C_6$-$C_{18}$ aryl;
wherein the $C_1$-$C_{10}$ alkyl is optionally substituted with one or more substituents independently selected from the group consisting of halogen, CN, $NO_2$, acyl, C(O)amino, C(O)OH, C(O)O(alkyl), C(O)O(cycloalkyl), C(O)O(heterocyclyl), C(O)O(aryl), C(O)O(heteroaryl), amino, alkylamino, amino (acyl), amino-C(O)amino, amino-C(O)OH, amino-C(O)O(alkyl), amino-C(O)O(cycloalkyl), amino-C(O)O(heterocyclyl), amino-C(O)O(aryl), amino-C(O)O(heteroaryl), amino-S(O)$_2$alkyl, amino-S(O)$_2$amino, amino-S(O)$_2$(alkylamino), amino-S(O)$_2$ (acylamino), amino-S(O)$_2$OH, amino-S(O)$_2$O(alkyl), amino-S(O)$_2$O(cycloalkyl), amino-S(O)$_2$O(heterocyclyl), amino-S(O)$_2$O(aryl), amino-S(O)$_2$O(heteroaryl), OH, O(alkyl), O(acyl), OC(O)amino, OC(O)OH, OC(O)O(alkyl), OC(O)O(cycloalkyl), OC(O)O(heterocyclyl), OC(O)O(aryl), OC(O)O(heteroaryl), OS(O)$_2$alkyl, OS(O)$_2$amino, OS(O)$_2$ (alkylamino), OS(O)$_2$ (acylamino), OS(O)$_2$OH, OS(O)$_2$O(alkyl), OS(O)$_2$O(cycloalkyl), OS(O)$_2$O(heterocyclyl), OS(O)$_2$O(aryl), OS(O)$_2$O(heteroaryl), SH, S(alkyl), S(acyl), S(cycloalkyl), S(heterocyclyl), S(aryl), S(heteroaryl), S(O)alkyl, S(O)acyl, S(O)cycloalkyl, S(O)heterocyclyl, S(O) aryl, S(O)heteroaryl, S(O)$_2$alkyl, S(O)$_2$acyl, S(O)$_2$amino, S(O)$_2$ (alkylamino), S(O)$_2$ (acylamino), S(O)$_2$OH, S(O)$_2$O(alkyl), S(O)$_2$O(cycloalkyl), S(O)$_2$O(heterocyclyl), S(O)$_2$O(aryl), S(O)$_2$O(heteroaryl), S(O)$_2$cycloalkyl, S(O)$_2$heterocyclyl, S(O)$_2$aryl, S(O)$_2$heteroaryl, cycloalkyl, heterocyclyl, aryl, and heteroaryl; and
wherein the $C_6$-$C_{18}$ aryl is optionally substituted with one or more substituents independently selected from the group consisting of halogen, CN, $NO_2$, $C_1$-$C_{10}$ alkyl, $C_2$-$C_{10}$ alkenyl, $C_2$-$C_{10}$ alkynyl, acyl, C(O)amino, C(O)OH, C(O)O(alkyl), C(O)O(cycloalkyl), C(O)O(heterocyclyl), C(O)O(aryl), C(O)O(heteroaryl), amino, alkylamino, amino (acyl), amino-C(O)amino, amino-C(O)OH, amino-C(O)O(alkyl), amino-C(O)O(cycloalkyl), amino-C(O)O(heterocyclyl), amino-C(O)O(aryl), amino-C(O)O(heteroaryl), amino-S(O)$_2$alkyl, amino-S(O)$_2$amino, amino-S(O)$_2$ (alkylamino), amino-S(O)$_2$ (acylamino), amino-S(O)$_2$OH, amino-S(O)$_2$O(alkyl), amino-S(O)$_2$O(cycloalkyl), amino-S(O)$_2$O(heterocyclyl), amino-S(O)$_2$O(aryl), amino-S(O)$_2$O(heteroaryl), OH, O(alkyl), O(acyl), OC(O)amino, OC(O)OH, OC(O)O(alkyl), OC(O)O(cycloalkyl), OC(O)O(heterocyclyl), OC(O)O(aryl), OC(O)O(heteroaryl), OS(O)$_2$alkyl, OS(O)$_2$amino, OS(O)$_2$ (alkylamino), OS(O)$_2$ (acylamino), OS(O)$_2$OH, OS(O)$_2$O(alkyl), OS(O)$_2$O(cycloalkyl), OS(O)$_2$O(heterocyclyl), OS(O)$_2$O(aryl), OS(O)$_2$O(heteroaryl), SH, S(alkyl), S(acyl), S(cycloalkyl), S(heterocyclyl), S(aryl), S(heteroaryl), S(O)alkyl, S(O)acyl, S(O)cycloalkyl, S(O)heterocyclyl, S(O)aryl, S(O)heteroaryl, S(O)$_2$alkyl, S(O)$_2$acyl, S(O)$_2$amino, S(O)$_2$ (alkylamino), S(O)$_2$ (acylamino), S(O)$_2$OH, S(O)$_2$O(alkyl), S(O)$_2$O(cycloalkyl), S(O)$_2$O(heterocyclyl), S(O)$_2$O(aryl), S(O)$_2$O(heteroaryl), S(O)$_2$cycloalkyl, S(O)$_2$heterocyclyl, S(O)$_2$aryl, S(O)$_2$heteroaryl, cycloalkyl, heterocyclyl, aryl, and heteroaryl;

$R_2$ is $C_1$-$C_{10}$ alkyl or $C_6$-$C_{18}$ aryl;

wherein the $C_1$-$C_{10}$ alkyl is optionally substituted with one or more substituents independently selected from the group consisting of halogen, CN, NO$_2$, acyl, C(O)amino, C(O)OH, C(O)O(alkyl), C(O)O(cycloalkyl), C(O)O(heterocyclyl), C(O)O(aryl), C(O)O(heteroaryl), amino, alkylamino, amino (acyl), amino-C(O)amino, amino-C(O)OH, amino-C(O)O(alkyl), amino-C(O)O(cycloalkyl), amino-C(O)O(heterocyclyl), amino-C(O)O(aryl), amino-C(O)O(heteroaryl), amino-S(O)$_2$alkyl, amino-S(O)$_2$amino, amino-S(O)$_2$ (alkylamino), amino-S(O)$_2$ (acylamino), amino-S(O)$_2$OH, amino-S(O)$_2$O(alkyl), amino-S(O)$_2$O(cycloalkyl), amino-S(O)$_2$O(heterocyclyl), amino-S(O)$_2$O(aryl), amino-S(O)$_2$O(heteroaryl), OH, O(alkyl), O(acyl), OC(O)amino, OC(O)OH, OC(O)O(alkyl), OC(O)O(cycloalkyl), OC(O)O(heterocyclyl), OC(O)O(aryl), OC(O)O(heteroaryl), OS(O)$_2$alkyl, OS(O)$_2$amino, OS(O)$_2$ (alkylamino), OS(O)$_2$OH, OS(O)$_2$ (acylamino), OS(O)$_2$O(alkyl), OS(O)$_2$O(cycloalkyl), OS(O)$_2$O(heterocyclyl), OS(O)$_2$O(aryl), OS(O)$_2$O(heteroaryl), SH, S(alkyl), S(acyl), S(cycloalkyl), S(heterocyclyl), S(aryl), S(heteroaryl), S(O)alkyl, S(O)acyl, S(O)cycloalkyl, S(O)heterocyclyl, S(O)aryl, S(O)heteroaryl, S(O)$_2$alkyl, S(O)$_2$acyl, S(O)$_2$amino, S(O)$_2$ (alkylamino), S(O)$_2$ (acylamino), S(O)$_2$OH, S(O)$_2$O(alkyl), S(O)$_2$O(cycloalkyl), S(O)$_2$O(heterocyclyl), S(O)$_2$O(aryl), S(O)$_2$O(heteroaryl), S(O)$_2$cycloalkyl, S(O)$_2$heterocyclyl, S(O)$_2$aryl, S(O)$_2$heteroaryl, cycloalkyl, heterocyclyl, aryl, and heteroaryl; and wherein the $C_6$-$C_{18}$ aryl is optionally substituted with one or more substituents independently selected from the group consisting of halogen, CN, NO$_2$, $C_1$-$C_{10}$ alkyl, $C_2$-$C_{10}$ alkenyl, $C_2$-$C_{10}$ alkynyl, acyl, C(O)amino, C(O)OH, C(O)O(alkyl), C(O)O(cycloalkyl), C(O)O(heterocyclyl), C(O)O(aryl), C(O)O(heteroaryl), amino, alkylamino, amino (acyl), amino-C(O)amino, amino-C(O)OH, amino-C(O)O(alkyl), amino-C(O)O(cycloalkyl), amino-C(O)O(heterocyclyl), amino-C(O)O(aryl), amino-C(O)O(heteroaryl), amino-S(O)$_2$alkyl, amino-S(O)$_2$amino, amino-S(O)$_2$ (alkylamino), amino-S(O)$_2$ (acylamino), amino-S(O)$_2$OH, amino-S(O)$_2$O(alkyl), amino-S(O)$_2$O(cycloalkyl), amino-S(O)$_2$O(heterocyclyl), amino-S(O)$_2$O(aryl), amino-S(O)$_2$O(heteroaryl), OH, O(alkyl), O(acyl), OC(O)amino, OC(O)OH, OC(O)O(alkyl), OC(O)O(cycloalkyl), OC(O)O(heterocyclyl), OC(O)O(aryl), OC(O)O(heteroaryl), OS(O)$_2$alkyl, OS(O)$_2$amino, OS(O)$_2$ (alkylamino), OS(O)$_2$ (acylamino), OS(O)$_2$OH, OS(O)$_2$O(alkyl), OS(O)$_2$O(cycloalkyl), OS(O)$_2$O(heterocyclyl), OS(O)$_2$O(aryl), OS(O)$_2$O(heteroaryl), SH, S(alkyl), S(acyl), S(cycloalkyl), S(heterocyclyl), S(aryl), S(heteroaryl), S(O)alkyl, S(O)acyl, S(O)cycloalkyl, S(O)heterocyclyl, S(O)aryl, S(O)heteroaryl, S(O)$_2$alkyl, S(O)$_2$acyl, S(O)$_2$amino, S(O)$_2$ (alkylamino), S(O)$_2$ (acylamino), S(O)$_2$OH, S(O)$_2$O(alkyl), S(O)$_2$O(cycloalkyl), S(O)$_2$O(heterocyclyl), S(O)$_2$O(aryl), S(O)$_2$O(heteroaryl), S(O)$_2$cycloalkyl, S(O)$_2$heterocyclyl, S(O)$_2$aryl, S(O)$_2$heteroaryl, cycloalkyl, heterocyclyl, aryl, and heteroaryl; or $R_1$ and $R_2$, taken together with the nitrogen atom to which they are attached, form a heteroaryl, wherein the heteroaryl is substituted with one or more substituents independently selected from the group consisting of halogen, CN, NO$_2$, $C_1$-$C_{10}$ alkyl, $C_2$-$C_{10}$ alkenyl, $C_2$-$C_{10}$ alkynyl, acyl, C(O)amino, C(O)OH, C(O)O(alkyl), C(O)O(cycloalkyl), C(O)O(heterocyclyl), C(O)O(aryl), C(O)O(heteroaryl), alkylamino, amino (acyl), amino-C(O)amino, amino-C(O)OH, amino-C(O)O(alkyl), amino-C(O)O(cycloalkyl), amino-C(O)O(heterocyclyl), amino-C(O)O(aryl), amino-C(O)O(heteroaryl), amino-S(O)$_2$alkyl, amino-S(O)$_2$amino, amino-S(O)$_2$ (alkylamino), amino-S(O)$_2$ (acylamino), amino-S(O)$_2$OH, amino-S(O)$_2$O(alkyl), amino-S(O)$_2$O(cycloalkyl), amino-S(O)$_2$O(heterocyclyl), amino-S(O)$_2$O(aryl), amino-S(O)$_2$O(heteroaryl), OH, O(alkyl), O(acyl), OC(O)amino, OC(O)OH, OC(O)O(alkyl), OC(O)O(cycloalkyl), OC(O)O(heterocyclyl), OC(O)O(aryl), OC(O)O(heteroaryl), OS(O)$_2$alkyl, OS(O)$_2$amino, OS(O)$_2$ (alkylamino), OS(O)$_2$ (acylamino), OS(O)$_2$O(alkyl), OS(O)$_2$O(cycloalkyl), OS(O)$_2$OH, OS(O)$_2$O(heterocyclyl), OS(O)$_2$O(aryl), OS(O)$_2$O(heteroaryl), SH, S(alkyl), S(acyl), S(cycloalkyl), S(heterocyclyl), S(aryl), S(heteroaryl), S(O)alkyl, S(O)acyl, S(O)cycloalkyl, S(O)heterocyclyl, S(O)aryl, S(O)heteroaryl, S(O)$_2$alkyl, S(O)$_2$acyl, S(O)$_2$amino, S(O)$_2$ (alkylamino), S(O)$_2$ (acylamino), S(O)$_2$OH, S(O)$_2$O(alkyl), S(O)$_2$O(cycloalkyl), S(O)$_2$O(heterocyclyl), S(O)$_2$O(aryl), S(O)$_2$O(heteroaryl), S(O)$_2$cycloalkyl, S(O)$_2$heterocyclyl, S(O)$_2$aryl, S(O)$_2$heteroaryl, cycloalkyl, heterocyclyl, aryl, and heteroaryl; and $R_3$ is H.

2. The compound of claim 1, wherein the compound is of Formula (Ib), Formula (Id), Formula (If), Formula (Ij) Formula (Il) or Formula (Im):

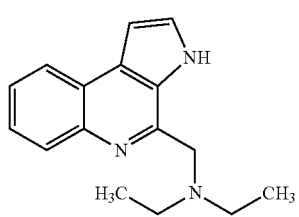

Formula (Ib)

25

-continued

Formula (Id)

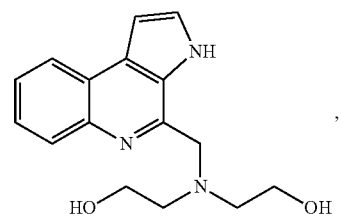

,

Formula (If)

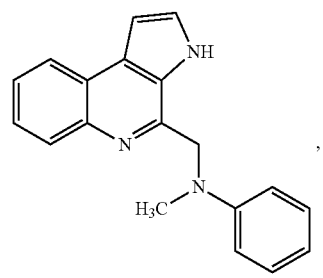

,

Formula (Ij)

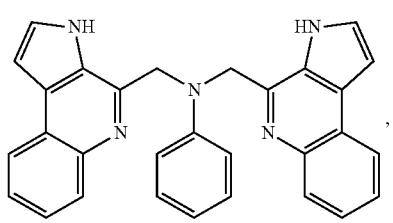

,

Formula (Il)

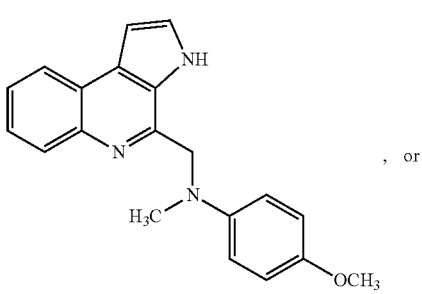

, or

Formula (Im)

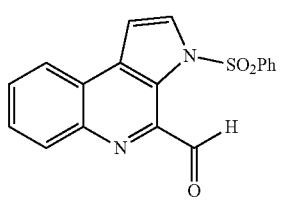

, or a pharmaceutically acceptable salt or stereoisomer thereof.

3. A pharmaceutical composition comprising a pharmaceutically acceptable carrier, diluent, or excipient and the compound of claim 1, or a pharmaceutically acceptable salt or stereoisomer thereof.

4. A pharmaceutical composition comprising a pharmaceutically acceptable carrier, diluent, or excipient and the compound of claim 2, or a pharmaceutically acceptable salt or stereoisomer thereof.

26

5. A process for preparing a compound of Formula (Im):

Formula (Im)

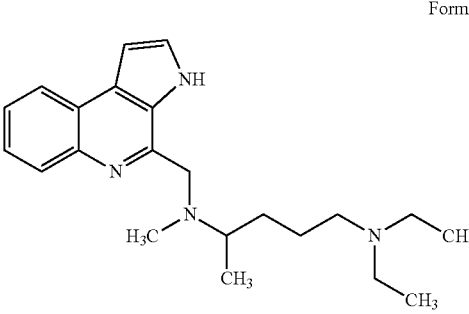

wherein the process comprises the following steps:
(A) heating selenium dioxide (SeO$_2$) and a compound of Formula (2):

Formula 2

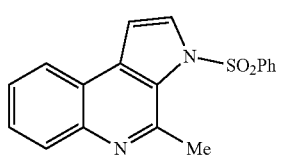

in a solvent at a temperature in the range of 60° C. to 80° C. for a period in the range of 10 hours to 14 hours, to afford a mixture comprising a compound of Formula (3):

Formula 3

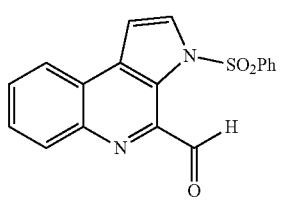

(B) stirring the reaction mixture provided in step (A) above and a compound of the following formula:

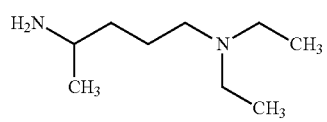

in the presence of 4 Å molecular sieves in a solvent at a temperature in the range of 25° C. to 30° C. for a period in the range of 20 hours to 24 hours, to afford a compound of Formula (4):

Formula 4

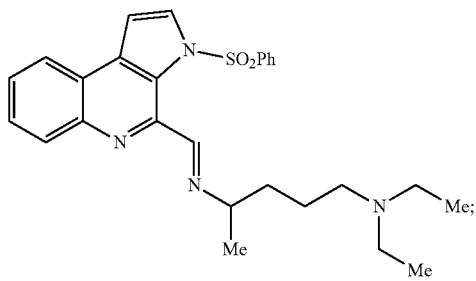

(C) reacting the compound of Formula (4) provided in step (B) above with sodium borohydride (NaBH₄) in a solvent, followed by refluxing the reaction mixture at a temperature in the range of 60° C. to 80° C. for a period in the range of 10 minutes to 20 minutes, to afford a compound of Formula (5):

Formula 5

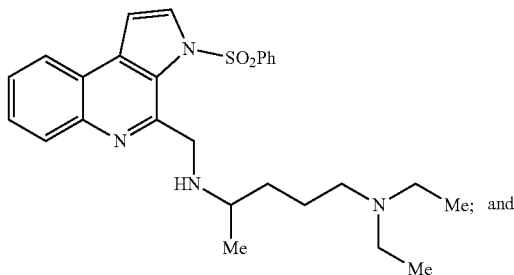

(D) (i) refluxing the reaction mixture provided in step (C) above in a solvent and formaldehyde at a temperature in the range of 60° C. to 80° C. for a period in the range of 20 minutes to 30 minutes;

(ii) cooling the reaction mixture to 0° C. and adding sodium borohydride (NaBH₄) at 0° C.; and (iii) stirring the reaction mixture at a temperature in the range of 25° C. to 30° C. for a period in the range of 20 hours to 24 hours, to afford the compound of Formula (Im):

Formula Im

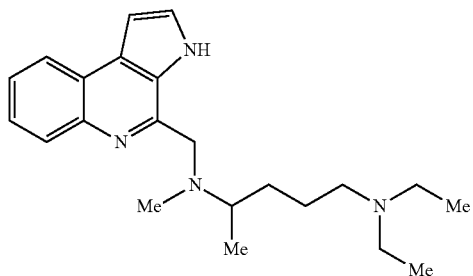

\* \* \* \* \*